(12) United States Patent
Bush et al.

(10) Patent No.: US 7,581,592 B1
(45) Date of Patent: Sep. 1, 2009

(54) SYSTEM AND METHOD FOR THE MANUFACTURE OF FUEL, FUELSTOCK OR FUEL ADDITIVES

(76) Inventors: Ronald R. Bush, 8645 Piney Creek Bend, Austin, TX (US) 78745; Bruce A. Johnson, 10221 Cama Valley Cove, Austin, TX (US) 78739

( * ) Notice: Subject to any disclaimer, the term of this patent is extended or adjusted under 35 U.S.C. 154(b) by 590 days.

(21) Appl. No.: 11/284,071

(22) Filed: Nov. 21, 2005

Related U.S. Application Data

(60) Provisional application No. 60/522,956, filed on Nov. 24, 2004.

(51) Int. Cl.
*E21B 43/24* (2006.01)

(52) U.S. Cl. ............... 166/302; 60/641.1; 60/641.2; 165/45; 166/272.1

(58) Field of Classification Search ............ 166/57, 166/246, 272.1, 272.6, 302; 60/641.1, 641.2; 165/45; 208/370; 405/129.1; 588/250; 435/262.5
See application file for complete search history.

(56) References Cited

U.S. PATENT DOCUMENTS

| | | | | |
|---|---|---|---|---|
| 3,330,356 A * | 7/1967 | Hottman | ............... | 166/57 |
| 3,554,285 A * | 1/1971 | Meldau | ............... | 166/258 |
| 3,606,999 A * | 9/1971 | Lawless | ............... | 423/659 |
| 3,954,140 A * | 5/1976 | Hendrick | ............... | 166/50 |
| 4,140,184 A * | 2/1979 | Bechtold et al. | ............... | 166/300 |
| 4,273,615 A * | 6/1981 | Hirbod | ............... | 376/275 |
| 4,455,374 A * | 6/1984 | Schwartz | ............... | 435/161 |
| 4,937,052 A * | 6/1990 | Takahashi et al. | ............... | 422/242 |
| 5,126,037 A * | 6/1992 | Showalter | ............... | 208/370 |
| 5,736,026 A * | 4/1998 | Patel et al. | ............... | 205/343 |
| 5,835,377 A | 11/1998 | Bush | | |
| 5,911,684 A * | 6/1999 | Shnell | ............... | 60/641.2 |
| 5,984,578 A | 11/1999 | Hanesian et al. | | |
| 6,236,942 B1 | 5/2001 | Bush | | |
| 6,284,143 B1 | 9/2001 | Kerfoot | | |
| 6,303,366 B1 | 10/2001 | Steffan et al. | | |
| 6,411,903 B2 | 6/2002 | Bush | | |
| 6,574,565 B1 | 6/2003 | Bush | | |
| 6,630,947 B1 | 10/2003 | Lieberman et al. | | |
| 6,688,388 B2 | 2/2004 | Zupanick | | |
| 6,754,589 B2 | 6/2004 | Bush | | |
| 6,754,689 B2 | 6/2004 | Bhushan et al. | | |
| 2003/0010652 A1 | 1/2003 | Hunt | | |
| 2006/0048770 A1* | 3/2006 | Meksvanh et al. | ............... | 126/620 |

\* cited by examiner

*Primary Examiner*—George Suchfield
(74) *Attorney, Agent, or Firm*—Johnson & Associates

(57) ABSTRACT

A method and system is provided relating to the production of ethanol or other renewable bio-fuels on a mass, large scale basis while maintaining a positive energy balance. In one example, the present invention relates to a system and method for the mass manufacture of fuel, fuel stock, or fuel additives by using dry or drying up hydrocarbon wells as a heat source in the manufacturing process. In one example, the distillation column is constructed from dried up oil wells.

3 Claims, 5 Drawing Sheets

SYSTEM AND METHOD FOR THE MANUFACTURE OF FUEL, FUELSTOCK OR FUEL ADDITIVES

CROSS REFERENCE TO RELATED APPLICATIONS

This application claims priority under 35 U.S.C. § 119/120 to commonly owned U.S. provisional patent application Ser. No. 60/522,956 filed on Nov. 24, 2004, entitled "SYSTEM AND METHOD FOR THE MANUFACTURE OF FUEL, FUELSTOCK OR FUEL ADDITIVES", which is incorporated by reference herein.

FIELD OF THE INVENTION

This invention relates to the manufacture of fuel, such as ethanol. In particular, this invention is drawn to a system and method for the manufacture of fuel, fuel stock, or fuel additives using dry or drying up hydrocarbon wells as a heat source in the manufacturing process.

BACKGROUND OF THE INVENTION

There is an ever increasing need for various forms of energy. One specific area of increasing need relates to alternative fuels, such as ethanol. While ethanol can currently be generated on a large scale today, there is a need for ways to manufacture ethanol more efficiently, and cheaply.

Since 1987, the U.S. Department of Energy (DOE) has sponsored more than 40 different colleges and high schools in Advanced Vehicle Technology competitions. These competitions are sponsored through Argonne National Laboratory which organizes and operates these competitions to accelerate the development and demonstration of technologies of interest to DOE and the automotive industry. FFV's (Flexible Fuel Vehicles), factory ready to use E-85 fuel which is 85% ethanol are now widely available. As of mid 2005 there have been over 2 million FFV's sold in the U.S. alone. Although still small, this indicates a substantial and increasing demand for ethanol.

A fuel cell is a device that can obtain 40 to 50% efficiency in conversion of a fuel into useable power (as opposed to approximately 18% efficiency for the average internal combustion engine). Some fuel cells use specialized molecular sieves made of complex polymers with anode/cathode properties, and others use expensive platinum catalysts. One of the main problems with any fuel cell is contamination of the membrane. It is a great advantage to use a fuel source which has been fully distilled; therefore, an ideal fuel for a fuel cell is ethanol. The use of fuel cell technology is also expanding. Regardless of which technology eventually dominates the automotive industry, the need for ethanol is expected to increase.

There has been a long existing need for the large-scale manufacture of fuel, fuel stock or fuel additives, and this need is or will continue to increase as the demand for energy increases, and the supply of conventional energy decreases.

SUMMARY OF THE INVENTION

An apparatus and method is provided for the manufacture of fuel, fuel stock, or fuel additives by using dry hydrocarbon wells in the manufacturing process. The use of dry hydrocarbon wells in the manufacturing process utilizes the inherent temperature and pressure characteristics of these dry wells to save on the large components of energy expenditure associated with fermentation and distillation. Furthermore, the construction of a subsurface manufacturing facility by using existing boreholes and reservoirs can be performed at a lower cost than constructing a surface plant that requires the manufacture of large amounts of pipe and tank capacity. The present invention takes a system wide view of the energy balance and cost equations to add value while reducing cost where possible.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
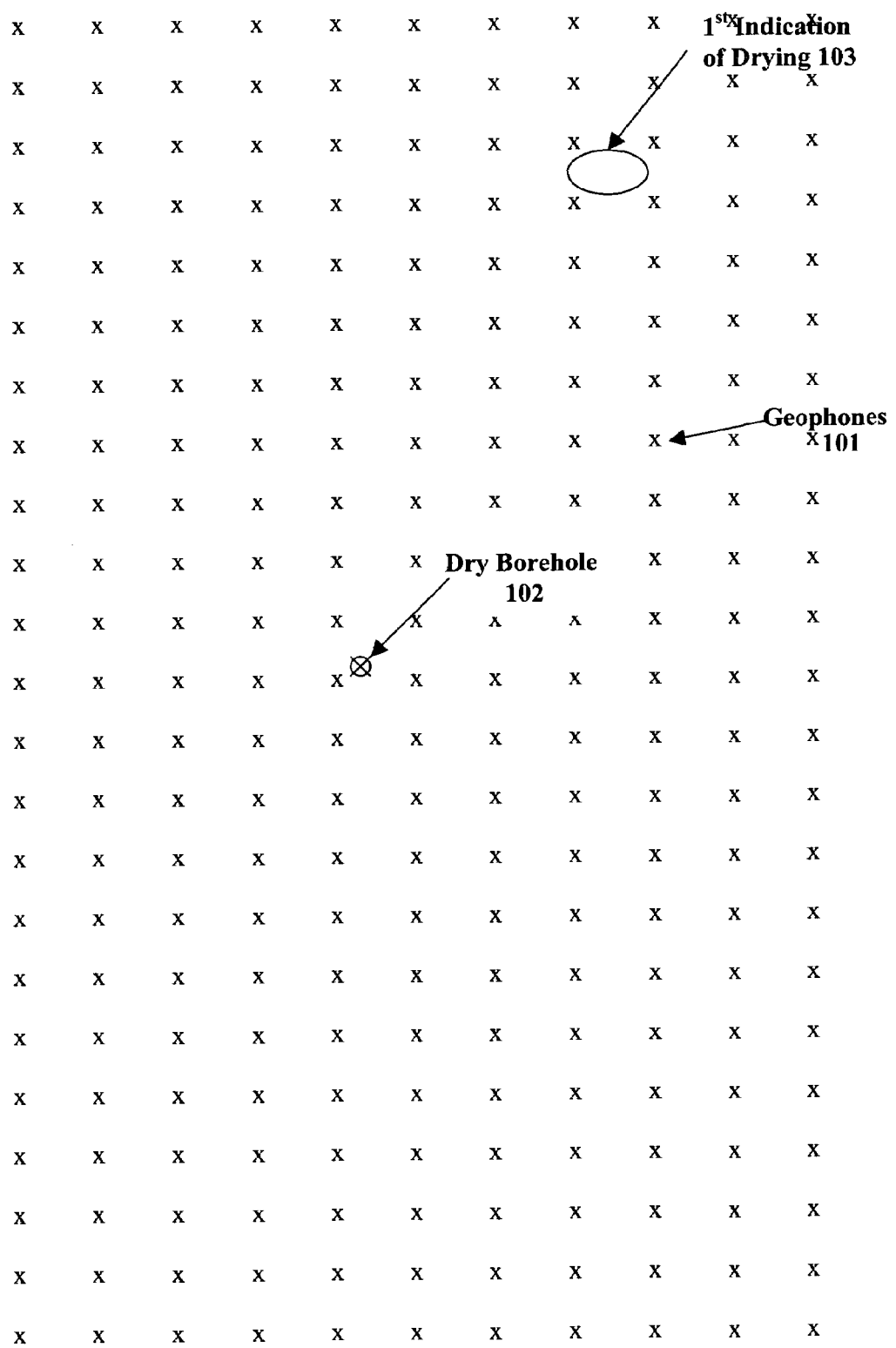
FIG. 1 shows geophones laid out in a traditional manner in an oil field with a schematic view of an initial take-down zone beginning to form.

Generally, the present invention relates to the manufacturing of fuel using "dry" hydrocarbon wells to provide the requisite temperature and pressure conditions. The present invention consists of providing an appropriate feedstock (i.e., generally, biomass feed stocks such as, but not limited to, corn, soybeans, other grains, ground cattle remains, algae, sewage, etc.), injecting this feedstock into a (first) dry or drying up hydrocarbon well, producing ethanol or a fuel stock containing ethanol, a fuel additive, from either the (first) dry or drying up hydrocarbon well or from a (second) dry or drying up hydrocarbon well either in the same take-down zone as the first dry or drying up well or in a well or wells in a separate take down zone. Generally, a take-down zone is that area from which a hydrocarbon borehole produces.

Methanol is also advocated as a future fuel. The system and method of the present invention is applicable in the case of any bio-fuel where heat is required in the manufacturing process. Furthermore, livestock feeds may also be generated as co-products in the bio-fuels manufacturing process described in the present invention. This occurs even without taking into account the energy used to make the co-products. Bio-fuels manufactured by the process of the present invention are net energy generators.

In one example, the invention relates to the manufacture of ethanol or alcohol from a feedstock such as corn, soybeans, algae, or other biomass. The total fuel energy expended in producing the alcohol—including fertilizing, farming, harvesting, transportation, fermentation, distillation, and distribution, as well as the fuel used in building the farm and fuel plant equipment—preferably should not exceed the energy contents of the product. As a result, the manufacture of ethanol may be treated as a system.

In two typical methods that are used for bio-fuel manufacturing, dry and wet milling, it has been recognized that the heat required for fermentation and distillation are the major energy consuming activities in the ethanol manufacturing process. Thermal and electrical powers are the main types of energy used in both types of milling plants. Currently most corn processing plants generate both electrical and thermal energy from burning coal or gas. A few plants generate only steam; electricity is purchased from a utility. Electricity is used mostly for grinding and drying corn. Thermal energy is used for fermentation, distillation, ethanol recovery, and dehydration.

If the geothermal energy and pressure in the dry or drying up boreholes is used in the fermentation and distillation activities, both the energy balance and cost are positively affected. Other energy and cost considerations, such as transportation, may also be addressed in the system wide view. The present invention discloses some of these considerations and presents solutions for their resolution.

Therefore, a method which has a positive energy balance is desired for the large scale mass production of bio-fuels. The present invention provides such a method. Furthermore, this description only describes a mass production system and process, but also describes other features that will facilitate this system.

The invention described below relates in general to a method and system for the manufacture of fuel, fuel stocks, or fuel additives using dry or drying up hydrocarbon wells in the manufacturing process. It is intended that the fuels described herein can be used in internal combustion engines, or for other applications. But the invention is not restricted in this regard. Flexible-fuel vehicles (FFV's) will provide a major market for the fuels manufactured by the processes of the present invention. FFV's are vehicles that can run on either regular gasoline or E-85 fuel, as an example. There is one fuel tank on a FFV and the driver can fill-it-up as they would with a regular vehicle. An on-board computer monitors the fuel mixtures and automatically adjusts the spark timing and fuel flow to the engine. Since this happens automatically, there is no special action required by the driver. Fuel cells are another example where ethanol might be used as a fuel. Any use of dry or drying up hydrocarbon wells in the manufacturing process of fuels, fuel stocks, or fuel additives falls within the scope of the present invention.

To help understand the invention, as well as to most efficiently practice the invention, it is helpful to have a basic understanding of hydrocarbon well boreholes and reservoirs. When an oil well is drilled into a hydrocarbon reservoir (containing oil, gas, both, etc.), the hydrocarbons are typically produced until it is no longer economically feasible to produce them. At this point, the well is considered "dry" or "depleted" (although the reservoir will typically still contain some hydrocarbons.

Figure 2:
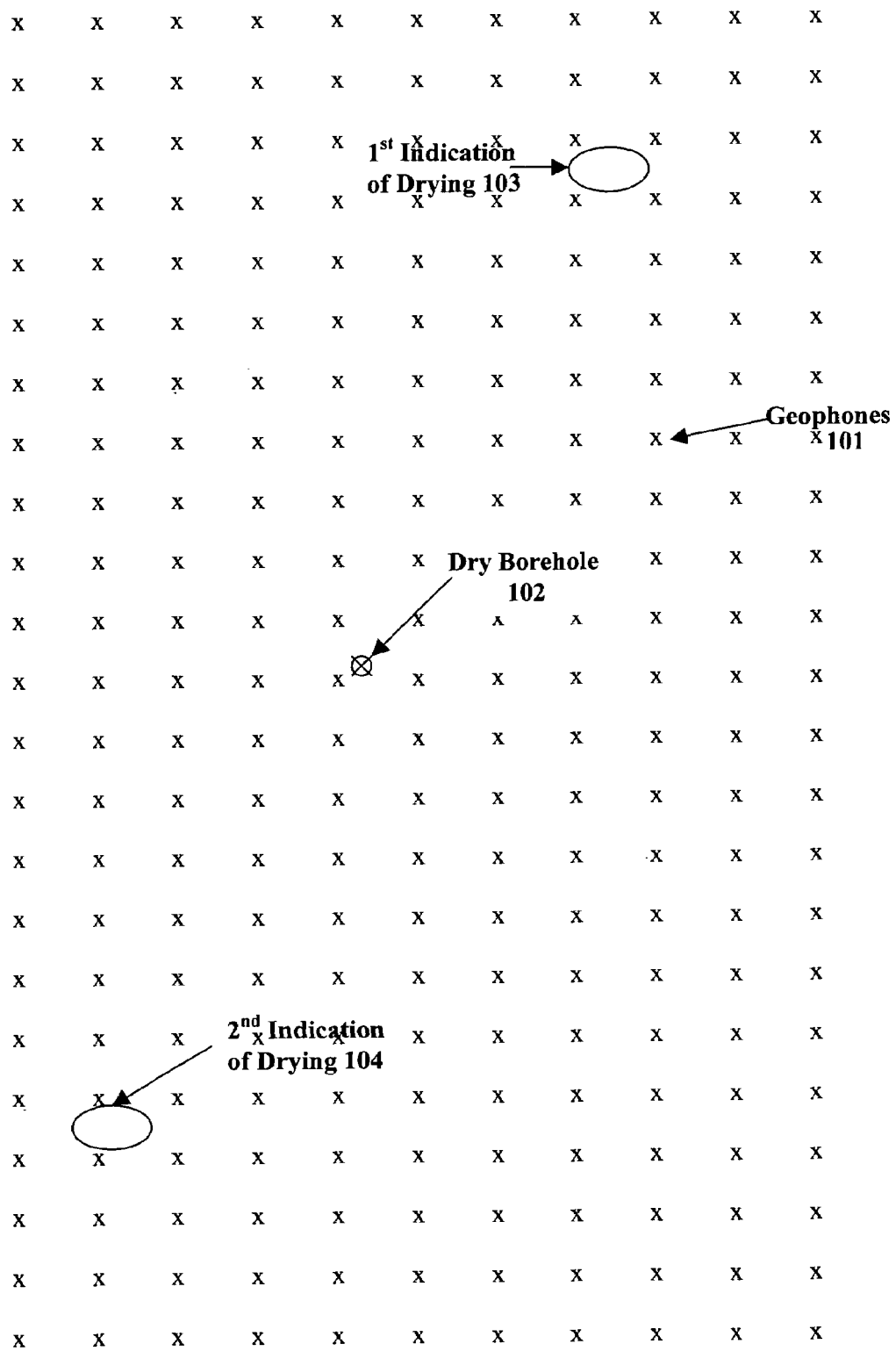
FIG. 2 shows the oil field of FIG. 1, with a second take-down zone beginning to form.
Figure 3:
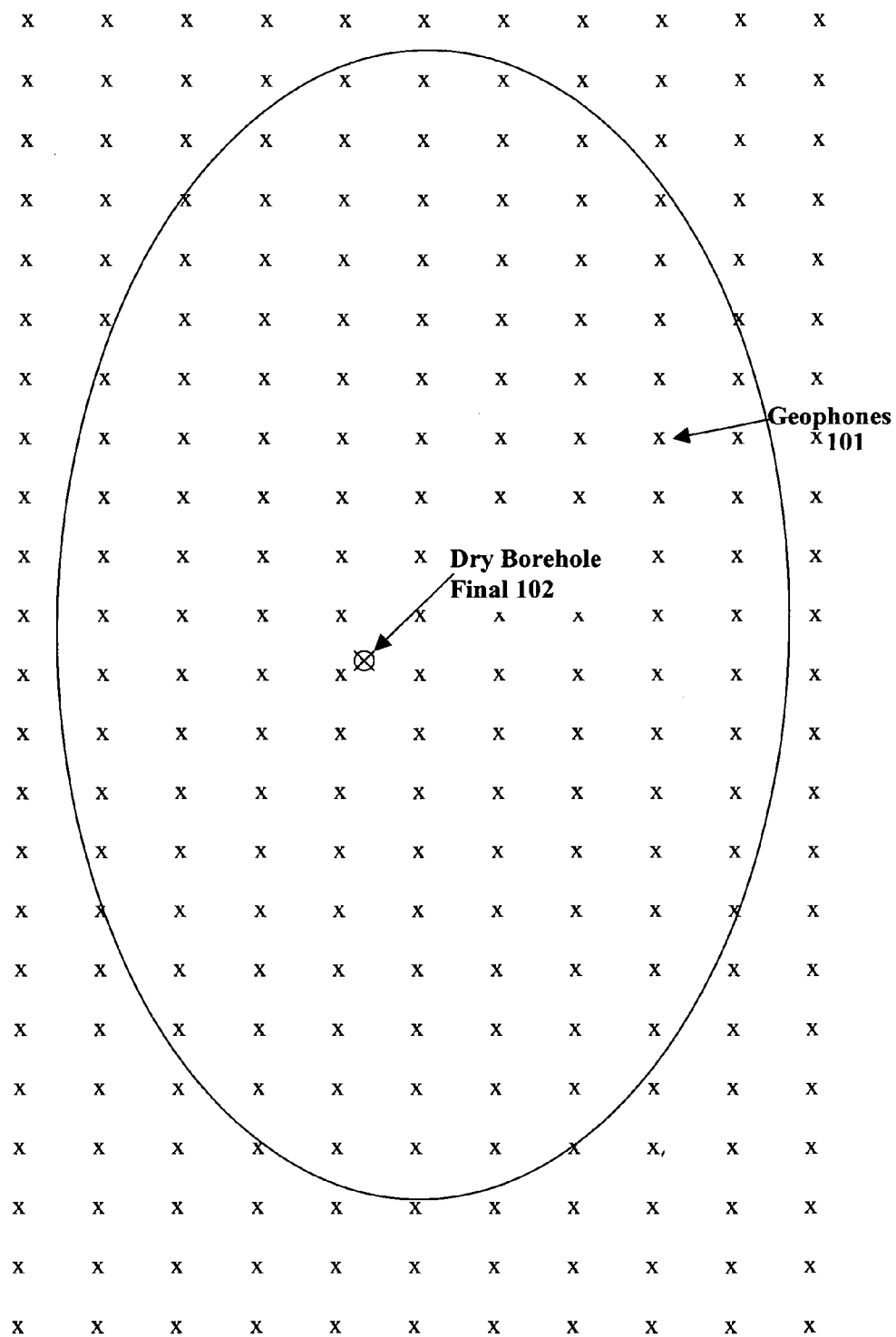
FIG. 3 shows the oil field of FIG. 1 after the borehole has dried up to where it is producing at a stripper level.

FIG. 1 is a schematic drawing of a traditional layout of geophones 101 in an oil field. In one example, a seismic shot can be taken shortly after the borehole 102 is drilled. The seismic data can be processed in any desired manner. For example, the seismic data can be processed pursuant to the teachings of U.S. Pat. No. 6,236,942 entitled "SYSTEM AND METHOD FOR DELINEATING SPATIALLY DEPENDENT OBJECTS, SUCH AS HYDROCARBON ACCUMULATIONS FROM SEISMIC DATA", which is incorporated by reference herein. Using the teachings of U.S. Pat. No. 6,236,942, an oil field can be accurately viewed, which is beneficial when determining where the present invention can most effectively be practiced. The initial take-down zone 103 is seen in the results. FIG. 1 is an exemplary schematic drawing; the take-down zone could be located anyplace in the field; and where the initial take-down zone begins to occur depends on the porosity and permeability throughout the formation. Another seismic shot, taken at a later time, is represented in the example of FIG. 2. FIG. 2 shows another take-down zone 104. Finally, in FIG. 3, the entire area drained by the borehole is signified by the area inside the oval. At this point, in this example, the hydrocarbon production has declined to a point where the oil well is not considered economically viable anymore.

The bottom-hole temperature of a depleted oil well (such as the well illustrated in FIG. 3) is known and is an approximate linear function of depth. Based on the observation of thousands of boreholes, it is estimated that the final take-down zone is on the average somewhere between 200 to 300 acres. Of course the size of a take-down zone varies.

Following is a brief overview of another exemplary application of the invention. In some examples, the invention is based on the utilization of dry or drying up hydrocarbon wells, primarily after incremental or enhanced production has taken place. However, in one example, the ethanol manufacturing process may be started before the well has been produced until it is commercially dry. In fact, in some circumstances, it may be advantageous to enrich existing hydrocarbons by the ethanol production process described in the present invention. For example, it might be found that it would be advantageous to add ethanol to crude oil before it is brought to the surface. The invention makes this possible.

While the invention can be practiced using one or more existing oil wells, another approach to the example described above is to drill a new well into the area that begins to dry up first. This position of initial dry up can be seen using the techniques taught U.S. Pat. No. 6,236,942, referenced above. Referring to FIG. 2, the initial take-down zones might be located at 103 and 104, as shown. After drilling a new well at 103 and/or 104, possibly with one as a side track of the other, it might be appropriate to inject a feedstock, such as corn mash, into this new well. This might be accomplished by using the temperature and pressure in the well to manufacture and add ethanol before or while producing the original target well 102.

This leads to the concept of "refining in the ground", i.e. changing the composition of hydrocarbon products before their final production. The process of moving a fuel stock toward a final fuel product while the fuel stock is still in the ground by utilizing the temperature and pressure characteristics that are a function of depth falls within the scope of the present invention. Thus, the improvement in the fuel characteristics of a hydrocarbon is considered to fall within the scope of the present invention.

An additional benefit of using dry or drying up hydrocarbon wells is that the locations of these wells are typically within the infrastructure of the hydrocarbon industry. Wells have been drilled, pipelines have been laid, Gas Oil Separation Plants (GOSP) exist, Refineries are generally in the area, and service companies and experienced oil-patch personnel are nearby, etc. All of these, as well as other unmentioned benefits, exist. The cost and time saved over other approaches to bringing bio-fuels into the marketplace is enormous.

Following is a brief overview of the present invention. The invention is based on the utilization of dry or drying up hydrocarbon wells for the manufacture of fuel, fuel stock, or fuel additives. An example of an invention includes creating subsurface manufacturing facilities and utilizing the in situ pressure and temperature characteristics of these facilities to manufacture fuel, fuel stock, or fuel additives. Dried up hydrocarbon reservoirs with their intrinsic porosity and permeability will yield ideal containers for the manufacturing process. In some examples, directional drilling and horizontal drilling, i.e. multilateral drilling techniques, may also be used to construct pseudo piping in the porous and permeable reservoir rock.

It is possible in some examples to have both surface as well as subsurface facilities. For example, part of the manufacturing process such as distillation might take place subsurface while the fermentation function might take place in surface facilities. Alternatively, dried up or drying up wells or sets of wells might be used for one function, say fermentation; while another dried up or drying up well or sets of wells might be used for another function such as distillation. The wells might even be at different depths to take advantage of differing temperature and pressure characteristics. Surface piping and/or subsurface pseudo piping might be utilized to connect these different wells or sets of wells. All such embodiments are considered to fall within the scope of the present invention.

Similarly, at the point where the co-product livestock feed needs to be dehydrated from the fermented feedstock, the intermediate product might be brought to the surface and spread out on plastic film, a grate, or other facility to dry in the sunlight. Alternatively thermal or hydrocarbon energy may be used from the dried or drying up hydrocarbon well in the dehydration process. All such embodiments fall within the scope of the invention.

Modern day hydrocarbon producers are in the process of applying horizontal and multilateral drilling techniques as well as electric submersible pumps (ESP's) in large volume. The ESP technology along with the hydrocarbon producer's knowledge of reservoir dynamics will be of great value in the manufacture of bio-fuels. The ESP technology is of great value since the fluid drive mechanisms found in newly discovered hydrocarbon fields will not be as prominent in the old fields.

One example of the present invention provides for the manufacture of ethanol using corn as a feedstock. However, those skilled in various arts will find many other applications of the present invention. Therefore, the partial suggestive list provided is only for purposes of illustration; and this list is not meant to be comprehensive as to the exact products that may be produced.

Likewise, various types of feedstocks can be used with the present invention. One example on this suggestive list might be the injection of raw sewage as a feedstock with methanol or methane as the expected product. This could reduce the cost of waste disposal while providing a fuel product. Yet another example on the list might be the use of ground up skeletal remains of cattle as a feedstock to produce a fuel stock that might be refined into a product similar to gasoline. The purpose of this approach would be the useful disposal of a problematic product that is now sometimes fed to cattle. The inclusion of cattle remains within livestock feed has the unfortunate consequence of increasing the probability of the spread of mad cow, or other diseases. The disposal of cattle remains while producing a fuel would have the added benefit of providing a safer food supply.

The present invention is presented in the form of examples, e.g., the production of ethanol from corn; however, ethanol can normally be also produced from most forms of starchy plant material such as wheat, barley or potatoes. Sugar cane is a particularly attractive feedstock. All such feed stocks, whether mentioned herein or not, are deemed to fall within the scope of this invention.

As an example, the State of California has investigated how its biomass resources are used and managed. Large quantities of dead/diseased trees and underbrush have accumulated in the forest, creating dangerous fuel loading which threatens human life and property. The use of this cellulose biomass in dry or drying up hydrocarbon wells falls within the scope of the present invention.

Following is a brief description of a typical process for creating ethanol. Of course, other processes may also be used. The first step is to break complex carbohydrates into simpler ones. Yeast is then added and the mixture is kept warm for perhaps several days until fermentation is complete. Air is kept out of the mixture to prevent oxidation of the ethanol. Enzymes in the yeast first convert carbohydrates like sucrose into even simpler ones like glucose and fructose, both $C_6H_{12}O_6$, and then convert these in turn into ethanol and carbon dioxide.

Figure 4:
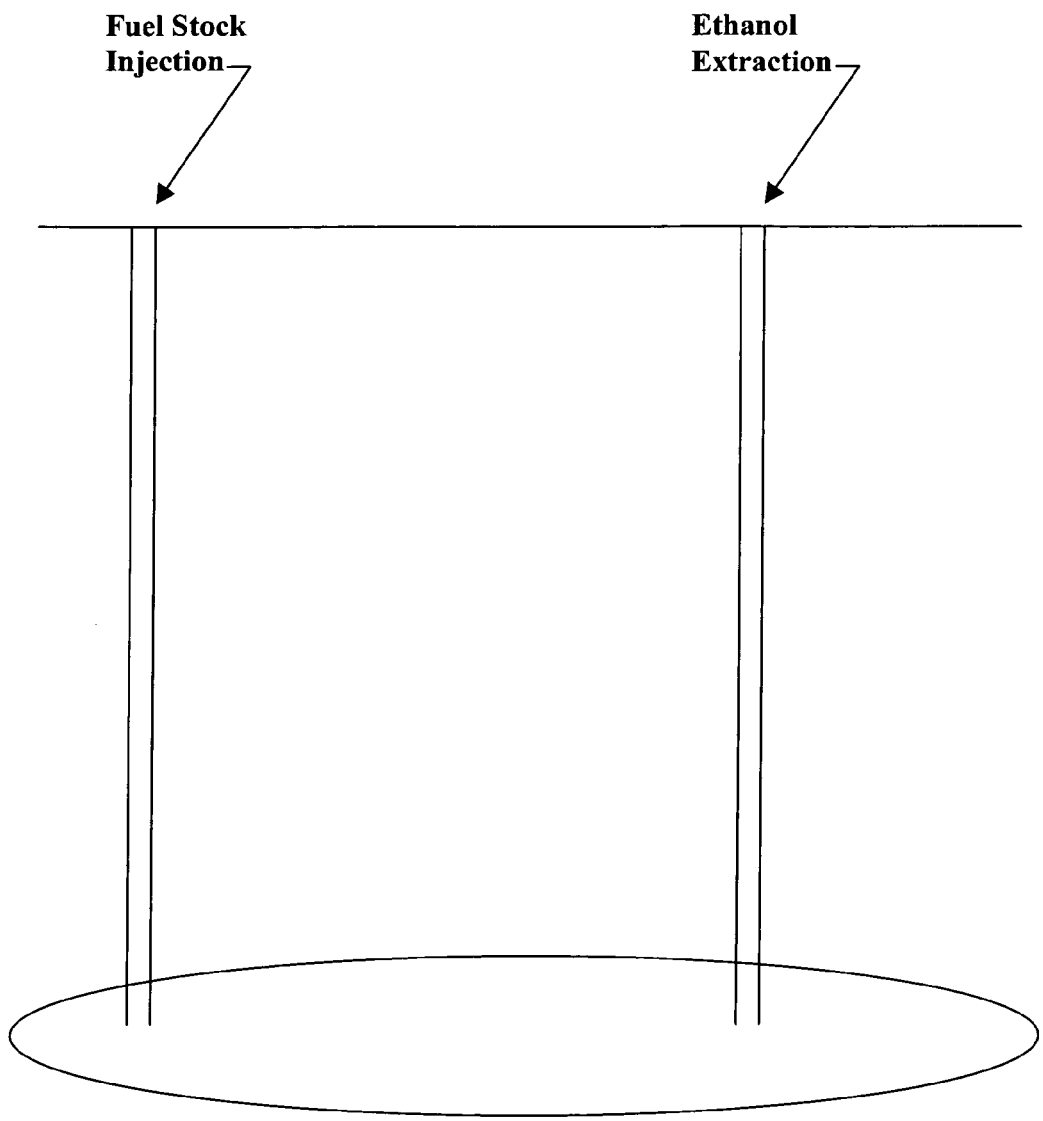
FIG. 4 is a cross sectional view showing the injection of a fuel stock in and ethanol extraction from the same formation using different boreholes.

Dry or drying up hydrocarbon reservoirs offer the air tight, pressurized, heated environments where this fermentation can take place. Yeast can be added to the corn mash either before injection or alternatively through boreholes in the same take down zone within a reservoir. Referring to FIG. 4, in one example, the injection of corn mash containing yeast might take place in the well labeled "Fuel Stock Injection". Production of ethanol might then take place from the dried up well labeled "Ethanol Extraction". In this example, both wells are in the same take-down zone. If desired, measures can be taken at each borehole to maintain a desired pressure. For example, valves at the boreholes can be closed to maintain a high pressure, or opened to release pressure. Likewise, the injected fuel stock can be injected at a pressure that prevents the pressure in the reservoir from falling below a desired level.

Figure 5:
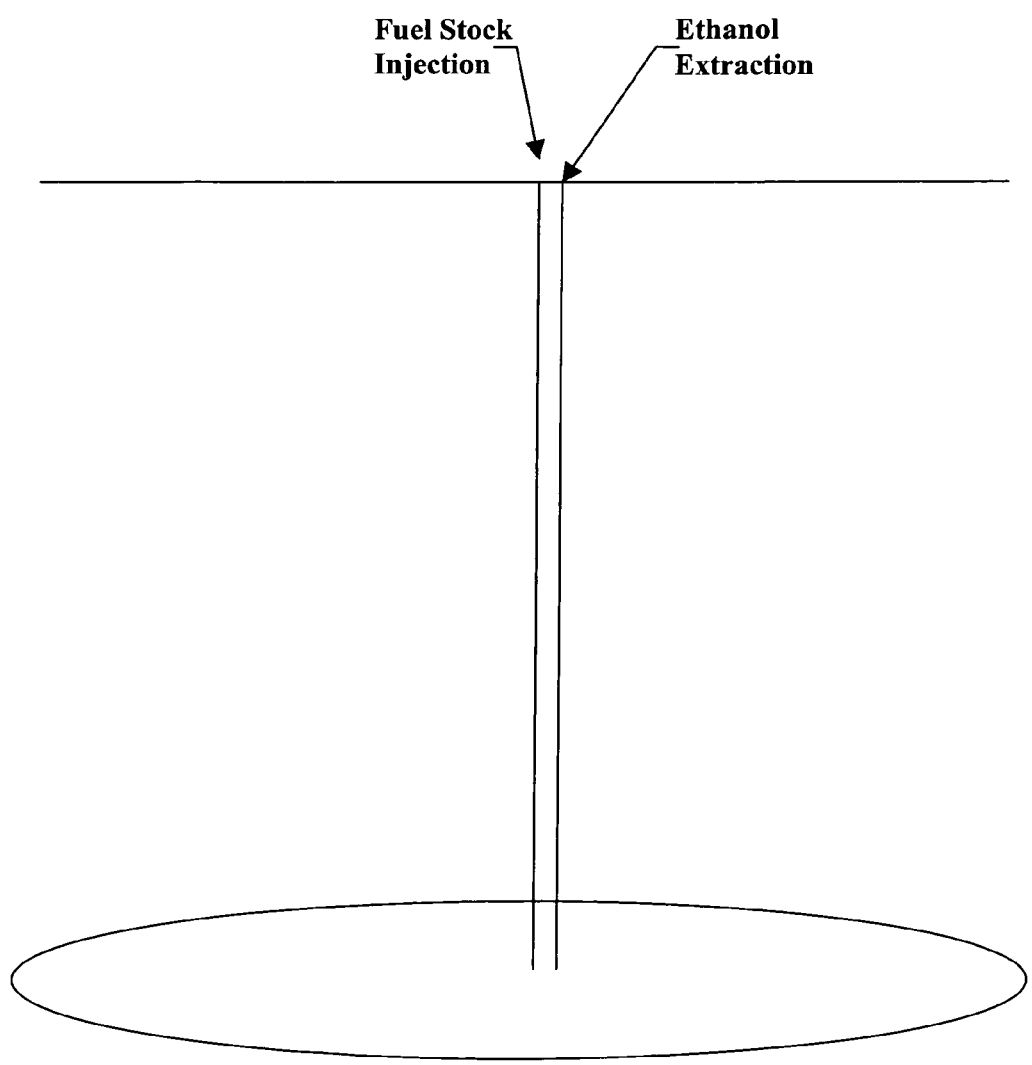
FIG. 5 is a cross sectional view showing fuel stock injection and ethanol extraction from the same borehole.

In another example, multiple take-down zones might be used in the manufacturing process. These take-down zones might be connected by sub-surface multilateral boreholes or alternately by surface piping. Metal catalysts might be inserted as borehole casing or surface piping. All such alternatives, whether mentioned explicitly herein or not, fall within the scope of this invention. In one example, down-hole hydrometers are used to measure the degree of fermentation at various stages in the manufacturing process. FIG. 5 shows an example where a single borehole is used. In this example, the same borehole is used to inject the feed stock, and to extract the ethanol.

Yeast is killed by ethanol concentrations in excess of about 15%, and this limits the purity of the ethanol that can be produced. To circumvent this problem, the ethanol is separated from the mixture by fractional distillation to give up to 96% pure ethanol. This fractional distillation can take place through the dry or drying up boreholes. In FIG. 4 this fractional distillation might take place in the borehole labeled "Ethanol Extraction." Where catalysts are required, borehole casing of the proper type can be used. A continuous flow process, where a stream of reactants is passed continuously through the catalyst is an efficient way of handling this process. The high temperatures and pressures that normally require a lot of energy input are a normal characteristic of boreholes at specific depths. Thus the major energy components of the ethanol manufacturing process are provided by the natural geothermal properties of the earth.

The present invention provides a method for the renewable manufacture of fuels, fuel stocks, or fuel additives. It is intended by the appended claims to cover all such applications as fall within the true spirit and scope of the present invention.

While the present invention has been described in the context of using dry or drying up hydrocarbon wells in the manufacturing process of fuels, fuel stocks, or fuel additives, the present invention is not limited to this particular application. The present invention may be utilized in any number of fields including but not limited to: the manufacture of synthetic motor oils, motor oil additives, livestock feeds, stocks for plastic manufacturing, disposal or remediation of waste products, etc.

One example in the application of the present invention relates to transportation. Referring to one example, barges can be used to move corn from corn producing states along the Mississippi River and its estuaries or tributaries to hydrocarbon well states such as Louisiana and Texas. In one example of the invention, where corn is converted to ethanol, the fermentation step might be carried out at least partially in transit. This might take place on connectable barges that when unconnected, can be stacked to float unloaded, or be stacked on flat bed trucks or railroad cars for return. In this situation, hydrometers, which measure the alcohol content of the corn mash, can be connected directly into the computer based manufacturing system. The state of fermentation versus the barge's position as measured by GPS can be handled by the computerized manufacturing system to coordinate subsequent activities. U.S. Pat. No. 5,835,377, entitled "Method and system for optimized material movement within a computer based manufacturing system utilizing global positioning systems" illustrates how computer control of a system might be used to optimize a process. This patent is incorporated by referenced herein.

The carts or barges used might, depending on the overall efficiency of the process, be used as milling and fermenting vehicles. If this is feasible from an overall system perspective, the computerized system will keep track of the location and state of fermentation of each cart/barge. In this case, paddles could be used to power a roller mill to reduce the corn into grain with a small percentage of fines. The power to rotate the paddles could be obtained by either going faster than the current, or by slowing the cart/barge down through the use of sails or dragging anchors. The objective of the computerization will be to produce the bio-fuel with a net energy gain at minimum cost.

In another example, the barges may have sails that can either add to or retard the velocity of the barge such that the barge is traveling faster than or less than the current of the river.

Continuing the transportation thought, reference is made to the example where livestock feed is a co-product. Here the transportation of corn for ethanol feedstock into a hydrocarbon well state such as Louisiana or Texas would have the additional effect of moving the co-produced livestock feed closer to a cattle producing area. On various ranches in Texas, for example, there are a large number of dry or drying up hydrocarbon wells and large numbers of cattle.

Various other examples and alternatives are possible with the invention.

In one example, a nanotechnology based molecular sieve may be used for the solid-liquid separation process. This molecular sieve might be used at several places in the bio-fuel manufacturing process.

As mentioned above, techniques for analyzing seismic data, such as those taught in the referenced U.S. Pat. No. 6,236,942, can be used to determine optimal hydrocarbon reservoirs to use to practice the present invention. These techniques may utilize 4-D seismic (i.e. carried out with time as the fourth dimension) to analyze data. In fact, the vibration that produces the seismic shock wave may produce a mixing effect in the manufacturing process. The extent of this effect may need to be determined to see to what extent the manufacturing process can be enhanced while carrying out the subsurface imaging process.

When practicing the invention, while injecting feedstock, any desired additives, catalysts, or other substances in to one or more hydrocarbon wells, other offset wells may be used for the recovery process. Also, dried up hydrocarbon reservoirs can be used for storage of fuels, fuel stocks, fuel additives or co-products.

While most examples described above discuss the invention in the context of injecting the feed stock into a depleted hydrocarbon reservoir, other examples are also possible. For example, the ethanol production process can take place above ground, while the heat used by the process is extracted from the depleted hydrocarbon reservoir. In this example, water or other heat exchange fluid can be circulated into and out of the depleted reservoir. The energy from the heated fluid can then be used as an energy source in the ethanol production process.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

What is claimed is:

1. A method of producing ethanol using geothermal heat from a depleted hydrocarbon well comprising:
    providing a depleted hydrocarbon well having at least one borehole;
    injecting a biomass feed stock into the depleted hydrocarbon well;
    exposing the biomass feedstock to heat and pressure conditions conducive to a fermentation process, wherein geothermal heat present in the depleted hydrocarbon well is used in providing heat to the biomass feedstock to facilitate fermentation of the feedstock to produce ethanol.

2. The method of claim 1, wherein the feedstock is made from grain.

3. The method of claim 1, wherein the feedstock is made from any biomass.

* * * * *